United States Patent
Levecq (10) Patent No.: US 8,087,779 B2
(45) Date of Patent: Jan. 3, 2012

(54) PHASE MODULATION DEVICE FOR AN OPHTHALMIC INSTRUMENT, OPHTHALMIC INSTRUMENTS EQUIPPED WITH SUCH DEVICE, AND RELATED CALIBRATION METHOD

(75) Inventor: Xavier Levecq, Gif sur Yvette (FR)

(73) Assignee: Imagine Eyes, Orsay (FR)

( * ) Notice: Subject to any disclaimer, the term of this patent is extended or adjusted under 35 U.S.C. 154(b) by 0 days.

(21) Appl. No.: 12/528,273

(22) PCT Filed: Feb. 20, 2008

(86) PCT No.: PCT/FR2008/050285
§ 371 (c)(1),
(2), (4) Date: Jan. 22, 2010

(87) PCT Pub. No.: WO2008/113937
PCT Pub. Date: Sep. 25, 2008

(65) Prior Publication Data
US 2011/0001930 A1    Jan. 6, 2011

(30) Foreign Application Priority Data
Feb. 21, 2007 (FR) ................... 07 01249

(51) Int. Cl.
A61B 3/10 (2006.01)
A61B 3/00 (2006.01)
G02F 1/01 (2006.01)
(52) U.S. Cl. ......... 351/205; 351/200; 351/221; 359/279
(58) Field of Classification Search .......... 351/205–206, 351/200, 203, 215, 221, 246; 359/278–279, 359/238–239, 245, 299, 300–304
See application file for complete search history.

(56) References Cited

U.S. PATENT DOCUMENTS
| | | | |
|---|---|---|---|
| 6,595,642 B2 * | 7/2003 | Wirth | ............................. 351/211 |
| 6,964,480 B2 | 11/2005 | Levine | |
| 2008/0018855 A1 | 1/2008 | Larichev et al. | |
| 2008/0284979 A1 * | 11/2008 | Yee et al. | ...................... 351/209 |

FOREIGN PATENT DOCUMENTS
FR     2 866 551     2/2004

OTHER PUBLICATIONS
Iroshnikov et al.—Adaptive optics in ophthalmology—2006—Proc. of SPIE vol. 6284 62840B-1, 10 pp.

* cited by examiner

*Primary Examiner* — Dawayne Pinkney
(74) *Attorney, Agent, or Firm* — Greer, Burns & Crain, Ltd.

(57) ABSTRACT

A phase modulation device implemented in an ophthalmic instrument using a main light beam interacting with an eye, the device including: an apparatus for modulating the phase of the wave front of the main light beam, a controller for controlling the phase modulation apparatus following a modulation instruction, and an analyzer for analyzing the thus-performed modulation of the phase of the wave front of the main light beam, further including emitting a secondary light beam, an apparatus for directing the secondary light beam along an optical path to the modulation apparatus, then to the analyzer, and in that the optical path does not pass through the eye, and in that the controller and the analyzer receiving the modulated secondary light beam cooperate, during a stage called a learning stage, to supply data regarding the response of the phase modulation apparatus to a set of predetermined modulation instructions.

27 Claims, 5 Drawing Sheets

PHASE MODULATION DEVICE FOR AN OPHTHALMIC INSTRUMENT, OPHTHALMIC INSTRUMENTS EQUIPPED WITH SUCH DEVICE, AND RELATED CALIBRATION METHOD

This application is a U.S. National Stage under 35 U.S.C. §371 of International Application No. PCT/FR2008/050285, filed Feb. 20, 2008, which claims priority from French Patent Application No. 0701249, filed Feb. 21, 2007.

BACKGROUND

The present invention relates to a phase modulation device for an ophthalmic instrument using a light beam interacting with an eye. It also relates to ophthalmic instruments implementing such a device, as well as to a calibration process for these ophthalmic instruments.

The field of the invention is more particularly that of visual correction simulators and ophthalmic imaging devices, in particular for high-resolution retinal imaging.

Ophthalmic instruments, such as for example instruments for retinal imaging or for optical laser treatment on the retina, operate with a main beam intended to pass through the various optical elements (cornea, crystalline lens, etc.) of a patient's eye, either by a beam incident on the eye (case of optical treatment of the retina), or as a beam emerging from the eye (case of retinal imaging).

In all cases, aberrations of the different optical elements of the eye cause aberrations of the wave front of the main beam, which degrades the quality of the optical instrument. Thus, in the case of retinal imaging, the image loses resolution and, in the case of the optical treatment of the eye, the quality of focusing the laser on the retina is degraded.

It is known to combine these ophthalmic instruments with a system for correcting aberrations of the eye making it possible to correct the wave front of the main beam, i.e. to give the optical beam phase the closest possible shape to a predetermined shape making it possible to obtain optimal performances from the instrument.

Such a system can also be used in an ophthalmic instrument of the vision simulation type, the purpose of which is to show a patient the effects of different corrections (corrective lenses, contact lenses, refractive surgery) by making him "see" an image, the analysis beam incident on the eye of the patient being then corrected for the ocular aberrations and/or showing the optical effects induced by the phenomenon which it is desired to simulate.

Such a system for correcting aberrations, described for example in patent application FR 2 866 551, comprises a Shack Hartmann type analyzer for measuring aberrations of the eye and an optical device for modulating the phase of the wave front of the main beam, of deformable mirror or spatial light modulator type, and controlled for correcting the wave front as a function of measured aberrations of the eye. In these systems, control of the optical modulation device is calculated as a function of a desired phase modulation on the main beam.

In the case of a visual simulation appliance operating in a closed loop, the problem generally faced is the need to direct light into the patient's eye, resulting in dazzling and thus disturbance to the simulation process, as well as creating a sensation of ocular discomfort.

In order to overcome this problem of dazzling in a closed loop, it is possible to use an incident beam in a spectral field invisible to the eye, typically in the infrared, but this would then involve dependence on the chromatism effects linked to a significant wavelength discrepancy between the aberration measurements (carried out in the infrared spectra) and the visual stimulation (carried out in the visible spectrum). It could also be envisaged to operate the modulation means in an open loop (without feedback). In this case, no light is directed into the patient's eye, and consequently, no wave front measurement is possible since no light returns from the eye. Such an approach has the drawback of imperfection of the modulation means (linearity problem, hysteresis, temperature drift). The errors generated on the modulation by these defects are not compensated for by a feedback loop (closed loop) and thus degrade the results of the correction or simulation.

Moreover, a further problem resides in the need to provide a learning or calibration stage of the adaptive optics process, the periodicity of which typically depends on the precision and stability requirements of a given application. In practice, this learning stage is carried out by using an artificial eye, subject to the following restrictions: said artificial eye must have a very high optical quality and requires careful alignment in front of the instrument.

The problem also arises of overcoming aberrations of the optical system itself. In fact, in many applications in which it is desired to perform measurements of eye aberrations in order to carry out correction or simulation, it is important to overcome the aberrations of the optical system used, as it must be capable of distinguishing on the one hand, the aberrations of the optical system of the ophthalmic system and on the other hand, the aberrations arising from the eye. A single measurement of the system aberrations carried out during its set-up is generally insufficient to ensure that these aberrations are known over a long period (typically several months) due to their temperature-dependence. In fact, the phase shifter element is generally an optical element that is sensitive to the temperature of its environment. Thus awareness of, or overcoming, aberrations of the optical system of the appliance requires measurement under its operating conditions. In practice, this measurement must be carried out with strict regularity, and in the state of the art requires the use of an artificial eye.

Moreover, it may be found necessary to add further corrections when it is desired to simulate phase objectives, such as an intraocular lens or implant. Here again, there is a need to overcome aberrations of the ophthalmic simulation device. In fact, in order to be capable of generating, in the pupil of the eye, a phase modulation representing the desired modulation free of aberrations of the ophthalmic device's optical system, it is necessary to be able to overcome the aberrations of the latter.

The purpose of the invention is to overcome these problems by proposing an ophthalmic device in which a complete closed-loop adaptive optics process, also comprising a learning stage, can be easily implemented without the need for the frequent use of an artificial eye, without discomfort for patients and under optimal conditions for overcoming the aberrations, despite ambient temperature variations, non-linearities and hysteresis phenomena on the phase modulators.

SUMMARY OF THE INVENTION

This objective is achieved with a phase modulation device implemented in an ophthalmic instrument using a main light beam interacting with an eye, this device comprising:

means for modulating the phase of the wave front of said main light beam, means for controlling said phase modulation means following a modulation instruction, and means for analysing the thus-performed modulation of the phase of the wave front of said main light beam.

According to the invention, this device includes means for emitting a secondary light beam, means for directing the secondary light beam along an optical path to the modulation means then to the analysis means, and this optical path does not pass through the eye, and the control means and analysis means receiving the modulated secondary light beam cooperate, during a stage called a learning stage, in order to provide data regarding the response of the phase modulation means to a set of predetermined modulation instructions.

A phase modulation device is thus provided that makes it possible to carry out periodic calibrations of the ophthalmic instruments, without the need to illuminate the patient's eye or to use an artificial eye.

It should be noted that the secondary light beam used in the phase modulation device according to the invention can be emitted from a light source that is either internal or external to the ophthalmic instrument equipped in this way. This secondary light beam can be fully internal to the ophthalmic instrument, but it can equally well be provided that a part of the optical path of this secondary beam can be outside the instrument.

In the phase modulation device according to the invention, the secondary light beam is directed along an optical path that does not pass through the eye which is being examined. It is also provided that for a fraction of this secondary light beam, which can for example originate from a beam splitter, to follow another optical path which can itself pass through the eye.

In the case of an ophthalmic instrument in which the phase modulation means comprise a mirror which can be deformed by the action of a plurality of actuators, the control means and the wave front analysis means cooperate during the learning stage in order to set each actuator successively in motion and to store, for each actuator, the response of the wave front analysis means.

The phase modulation device according to the invention can advantageously comprise means for modifying the control applied to the modulation means, so as to reduce a discrepancy between the modulation instruction and the modulation carried out on the secondary beam.

The modulation means are preferably arranged to simultaneously modulate the phase of the wave front of the main beam and the phase of the wave front of the secondary beam according to a modulation instruction.

In a first range of uses of the phase modulation device according to the invention, corresponding to visual simulation instruments, the latter comprises means for projecting an image of a target onto the retina of the eye. The light rays originating from this target can advantageously constitute the main beam.

The modulation means are then controlled to simulate on the main beam a static correction integral with the eye, such as refractive surgery, or correction by a contact lens, a spectacles lens or an ocular implant.

A second range of uses of the phase modulation device according to the invention corresponds to high-resolution retinal imaging instruments, comprising means for illuminating the retina of the eye, means for detecting a light beam emerging from the eye and for forming an image of the retina, this emergent beam constituting the main beam.

A third range of uses of a phase modulation device according to the invention corresponds to instruments for the optical treatment of the retina of the eye comprising a laser source for emitting the main beam, and means for focussing the main beam onto the retina of the eye.

Use of a phase modulation device according to the invention can also be provided in an instrument for measuring aberrations of the eye, comprising means for measuring aberrations of the eye liable to interfere with the main beam, and means for calculating the modulation instruction as a function of the measured values of the aberrations of the eye.

In such an instrument, the means for measuring aberrations of the eye comprise means for emitting an illumination beam in order to form a secondary light source on the retina of the eye, this secondary source emitting a beam which emerges from the eye, and means for guiding this beam to means for measuring the phase of the wave front of this beam.

The ophthalmic instruments according to the invention can comprise means for measuring the movements of the eye, and means for calculating the modulation instruction as a function of the measured values of the movements of the eye.

These means for measuring the movements of the eye comprise, for example, means for measuring a lateral displacement of the pupil of the eye in relation to a predetermined position, means of illuminating the pupil of the eye, a matrix detector, and a lens forming the image of the pupil of the eye on the detector.

According to another aspect of the invention, a process is proposed for calibrating an ophthalmic device using a main light beam interacting with an eye and in which are implemented: (i) a phase modulation of the wave front of said main light beam by phase modulation means and (ii) an analysis of said wave front phase modulated in this way by phase analysis means.

This process is characterized in that it comprises, during a stage called a learning stage:
  emitting a secondary light beam which is subjected to said phase modulation then to said phase analysis, and
  a sequence of predetermined controls of said phase modulation means, and storage of phase analysis data in response to said modulation controls,
and in that the secondary light beam is directed along an optical path to said modulation means and to said phase analysis means, and in that said optical path does not pass through the eye.

The process according to the invention can be implemented in an apparatus in which the phase modulation means comprise a deformable mirror actuated by a plurality of actuators. The sequence of predetermined controls comprises controls for successively starting each actuator to move and for storing, for each actuator, the response of said wave front analysis means.

It could have seemed obvious, in order to limit the visual discomfort of a patient while ensuring effective control of a phase modulation device, to improve the enslavement process described in the document FR2 866 551 by using for the measurement of eye aberrations, a source of illumination that is invisible to the eye, typically at an infrared wavelength greater than 900 nanometers. However, due to the eye's chromatism, enslavement of the modulation means carried out in the infrared would not necessarily have been valid for the main beam if the latter had a different wavelength, typically in the visible spectrum. Moreover, use of a secondary beam interacting with the eye necessarily limits the flux available for the measurement due to eye safety standards. This suggests that this measurement is carried out with a low recurrence rate or with a phase analyzer having a reduced number of measurement points. In both cases, the quality of the enslavement is reduced.

The invention provides an ingenious way of enslaving the modulation means, because in the preferred case where a wavelength of the secondary beam is approximately equal to a wavelength of the main beam, it makes it possible to avoid both achromatism problems of the eye and of the set of optical elements used, including the phase modulation means, in particular in the case where the modulation means comprise a liquid-crystal phase modulator.

Preferably, a wavelength of the secondary beam is approximately equal to a wavelength of the main beam.

The calibration process according to the invention, implemented in an ophthalmic instrument comprising a primary source for generating a main light beam for illuminating the retina of an eye and a second source for generating a secondary light beam, comprises:

a step of measuring the aberrations of the optical system of the ophthalmic instrument, said primary source of illumination of the retina being switched on, a step of determining the position of the pupil of the eye during the step of measuring the aberrations, a step of switching off the primary source of illumination of the retina, a step of starting the second source for generating the secondary beam, this secondary beam being used in the learning stage, and a step of applying correction and/or simulation controls to the phase modulation means.

These steps can be automated as a whole, so that the operator of an ophthalmic instrument implementing such a process according to the invention can benefit from an automatic, optionally periodic, calibration of said instrument.

It can also be provided for the calibration process according to the invention to comprise an implementation of a fixation target, such as a micro-display, on which images or visual tests can be displayed, this fixation target being provided to give a patient a subjective measure of the effect of the correction and/or simulation.

This process can also include, prior to the step of measuring the aberrations, an initial learning step and a step of overcoming the aberrations of the optical system of the ophthalmic instrument.

The step of overcoming the aberrations of the optical system comprises, for example, enslaving the phase modulation means, which can be carried out in the form of a deformable mirror by a plurality of actuators, with reference to a set of instructions determined so as to correct the aberrations of the optical system.

DETAILED DESCRIPTION

Other advantages and features of the invention will become apparent from reading the detailed description of implementations and embodiments which are in no way limitative, and from the following attached drawings.

In order to simplify FIGS. 1 to 5, each light beam shown therein is represented diagrammatically by two light rays on the edges of said beam.

Firstly, with reference to FIGS. 1 and 2, a phase modulation device according to the invention will be described which is integrated into a vision simulation instrument and implementing a process according to the invention.

Such a device comprises a fixation path including a light source VF which, when illuminated, emits a test image intended to be viewed by a patient's eye. This light source typically comprises a micro-display (OLED or LCD or MEMS technology) on which different images or visual tests can be displayed. The test image is constituted by a set of light rays which form the main light beam FA of the device. The main light beam FA passes through a beam splitter C1, then is guided to means MD for modulating the phase of the wave front of the main beam. The beam splitter C1, like all the other beam splitters described below, can typically consist of a semi-reflective mirror or a dichroic filter. The modulation means MD intercept the main beam FA. The modulation means are preceded by an optical system S1, arranged so that the main beam FA is a parallel light beam when it is intercepted by the modulation means MD. The modulation means are connected to a control unit COM, which is connected to processing means TRT. These control means COM and processing means TRT typically comprise a central processing unit of a computer or a simple electronic card. The control means COM apply a control to the modulation means MD allowing the phase of the wave front of the main beam FA to be modified locally. The control is calculated by the processing means on the basis of a modulation instruction which corresponds to the desired modulation to be carried out by the modulation means on the main beam or any other beam intercepted by these means.

The optical modulation means MD comprise a deformable mirror constituted by a reflective surface which can be deformed by a set of actuators on which the main beam is incident, positioned substantially in a plane conjugated with the pupil of the eye, each actuator being controlled by the control unit in order to modulate the local phase of the wave front of the main beam. It is also possible to use a spatial light modulator (or SLM), for example, produced by an array of liquid crystal valves.

After its phase has been corrected by the deformable mirror, the main beam FA continues its optical path. It is reflected by beam splitters LM0 then LM1 before being focussed on the retina of the eye by a lens L1. The optical path of the main beam FA, starting from the source VF to the retina of the eye EYE, is shown in FIG. 1 by two dotted lines.

The device comprises means SI for emitting a measurement light beam FC. When it is emitted, the measurement light beam is guided to the modulation means MD, typically by a beam splitter LM2 situated on the optical path of the main beam between the modulation means MD and the beam splitter LM0. The beam splitter makes it possible to superimpose the portions of the optical paths of the secondary beam and the main beam situated between the beam splitter LM2 and the beam splitter C1. The modulation means MD thus intercept the secondary beam FC. The beam splitter LM2 is preceded by an optical system S2 arranged so that the secondary beam FC is a parallel light beam when it is intercepted by the modulation means MD. The modulation means are therefore arranged in order to locally correct or modulate the phase of the wave front of the secondary beam FC according to the modulation instruction corresponding to the control applied to the modulation means MD.

After modulation of its phase by the deformable mirror, the secondary beam FC continues its optical path. It passes through the optical system S1, is separated from the optical path of the main beam FA, by being reflected by the beam splitter C1, then passes through a lens L2 and is directed to optical measurement means MA arranged for measuring the phase of the wave front of the secondary beam in a given measurement plane PA. The measurement means MA, for example an analyzer of the Hartmann or Shack-Hartmann type, are connected to the processing means TRT which, in a known manner, establish the phase cartography of the secondary beam. A representation of this cartography can be displayed on a screen SCR.

The secondary beam FC is guided along an optical path such that it does not interact with the eye. The optical path of the secondary beam FC, which starts from the emission means SI and goes up to the measurement means MA, is shown in FIG. 1 by em dash-dot-dot lines. The wavelength of the secondary beam FC is approximately equal to the wavelength of the main beam FA, which makes it possible to avoid problems of chromatism of the eye and chromatism of the optical elements of the instrument, in particular possible chromatism of the phase modulation means MD. For the test image to be visible to the eye, the wavelength of the secondary beam FC and that of the main beam FA are situated in the visible, i.e. approximately 400 to 700 nanometers, or in the near infrared.

The processing means TRT are equipped with means for measuring the phase modulation carried out on the secondary beam by the modulation means MD, and in particular for comparing the phase modulation carried out on the secondary beam and the modulation instruction, said instruction corresponding to the desired modulation to be carried out by the modulation means on any beam intercepted by the latter. The processing means TRT are connected to the control unit and comprise means for modifying the control applied to the modulation means, in particular if the modulation carried out differs from the modulation instruction. Preferably, the modification is carried out to minimize a discrepancy between the modulation instruction and the modulation carried out on the secondary beam, preferably until the modulation carried out on the secondary beam is equal or at least approximately equal to the modulation instruction. The means of modifying the control therefore constitute a feedback system, having as input values the modulation instruction and measurement of the phase modulation carried out on the secondary beam by the modulation means, and as output value, the control calculated on the basis of the input values and applied to the modulation means. The measurement of the phase modulation carried out on the secondary beam by the modulation means can be calculated by the processing means as the difference between the measurement, by the measurement means MA, of the phase of the wave front of the secondary beam, and a value, stored in the processing means, of the phase of the wave front of the secondary beam as emitted.

The processing means TRT comprise means for determining the control by implementing a calculation algorithm comprising the modulation instruction as a variable. The means for modifying the control comprise means for calibrating the means of determining the control, and in particular for calibrating parameters used in the calculation algorithm, such as parameters which do not depend in a simple or linear fashion on the modulation instruction or parameters dependent on the ambient temperature.

Figure 5:
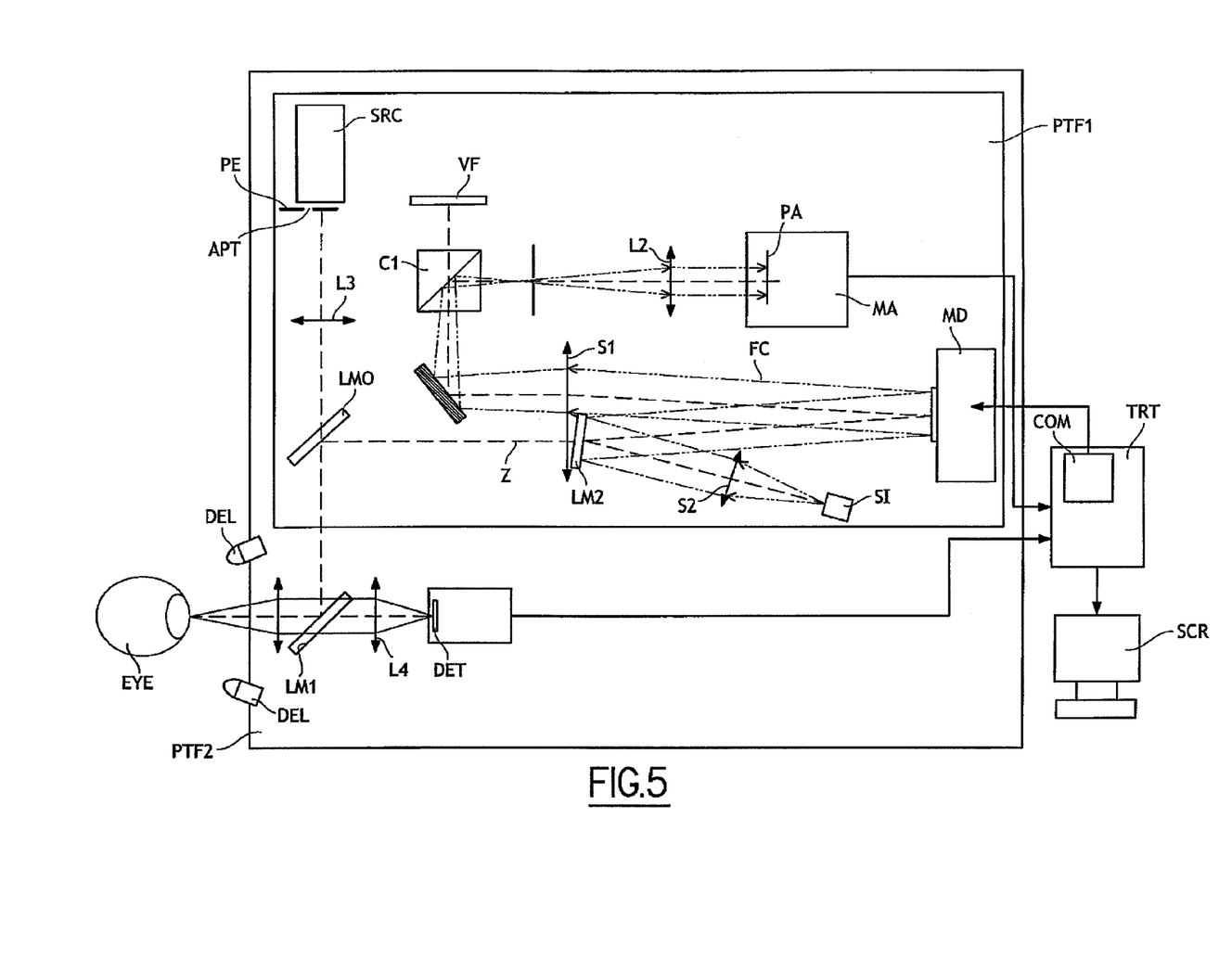
FIG. 5 shows the light beams implemented during a learning stage in the vision simulator of FIGS. 1 and 2.

With reference to FIG. 5, the learning or calibration stage of the adaptive optics loop consists of teaching the software how the phase actuated by each actuator or combination of actuators is modulated. This calibration can be considered as a constant of the system but experience shows that it is preferable, in order to maintain optimal performance, to carry out this learning stage regularly.

A simple but effective possibility for carrying out this learning stage in practice consists of moving the mirror, actuator by actuator, and for each actuator, storing the response of the analyzer.

Thus at the end of this learning stage the following relationship is obtained:

$$MI \cdot V = P$$

where
MI is a matrix of n (number of actuators) columns and m (numbers of illuminated microlenses ×2) lines. Column i contains the information in terms of local slopes of the influence of the actuator i.
The slopes are arranged arbitrarily: first the local slopes x, then the local slopes y.
A vector element is a local slope under a sub-pupil.
V is the voltages vector for controlling the deformable mirror
P is the vector of the slopes x and y at the focus of each sub-pupil.

At the end of this stage it is possible to predict what the analyzer will see if a control V is applied to the mirror.

The inverse is desired for the correction: it is desired to find the control to be applied to the mirror as a function of the vector of the measured slopes x and y. In fact a relationship is required of the type:

$$V = MC \cdot P$$

It is noted that MC is in fact the inverse of MI. MC is therefore obtained by numerical inversion of MI.

Figure 1:
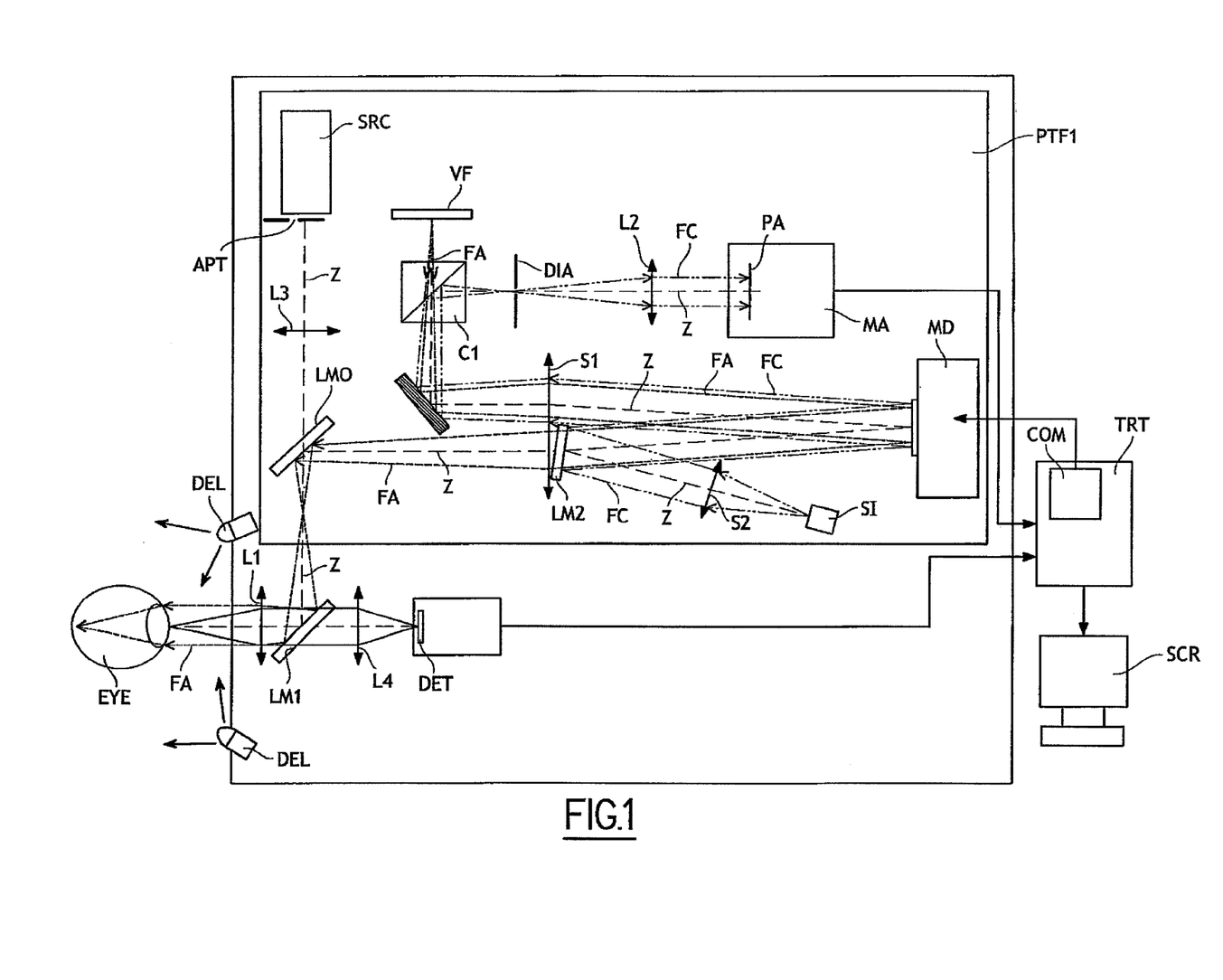
FIG. 1 shows a phase modulation device according to the invention, integrated into a vision simulation instrument and implementing the steps of the process according to the invention.
Figure 2:
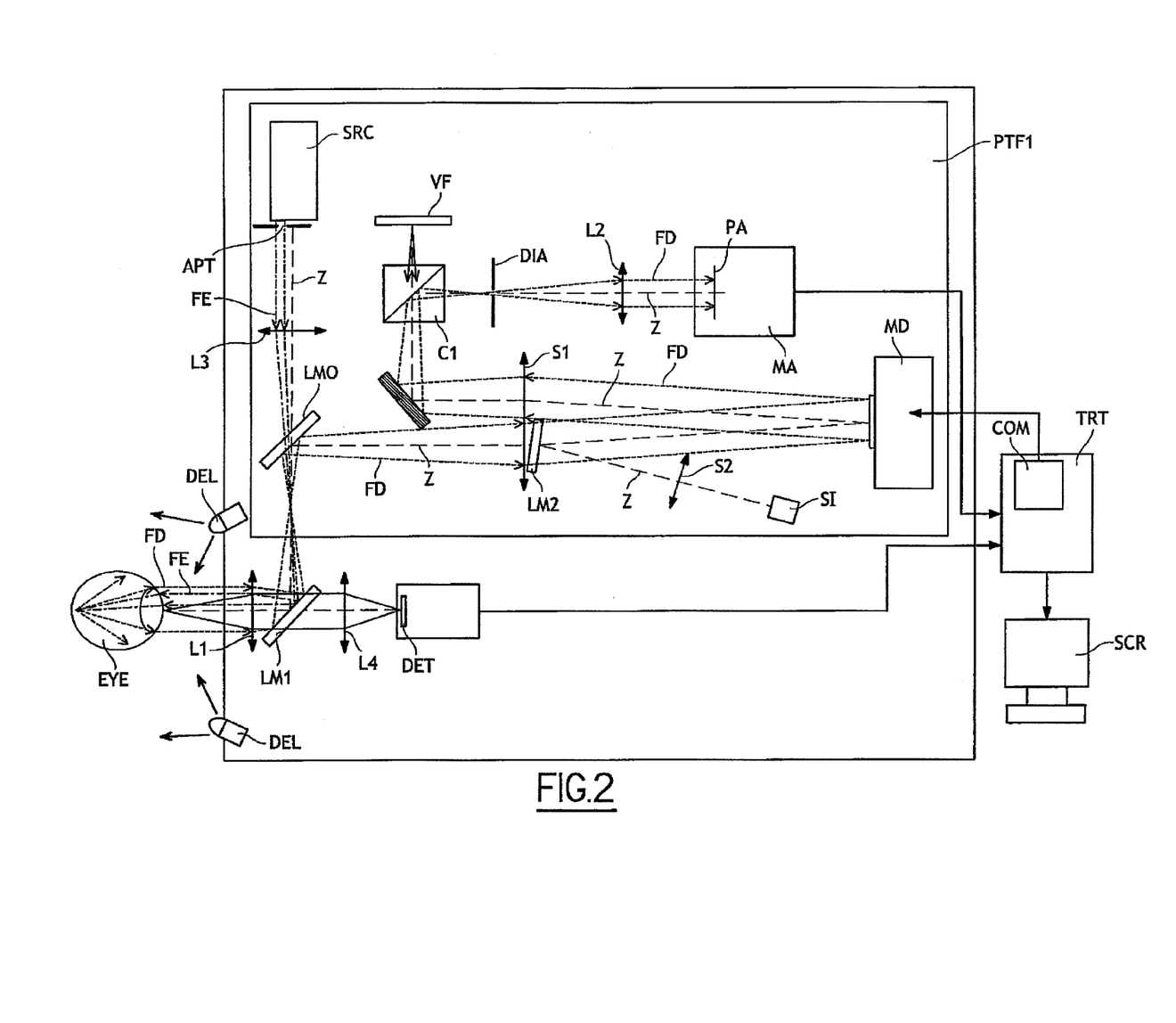
FIG. 2 shows the vision simulator of FIG. 1 implementing other steps of the process according to the invention.

An embodiment of the process according to the invention implemented in the vision simulator according to the invention shown in FIGS. 1 and 2 comprises the following steps:
controlling the modulation means according to the modulation instruction,
emitting the measurement light beam FC, the source SI being switched on,
modulating, according to the modulation instruction, the phase of the wave front of the secondary beam by the modulation means MD,
measuring the phase modulation carried out by the modulation means on the secondary beam, and
if the phase modulation carried out by the modulation means on the secondary beam is approximately equal to the modulation instruction, maintaining the control applied to the modulation means, or
if the phase modulation carried out by the modulation means on the secondary beam differs from the modulation instruction, modifying the control applied to the modulation means, comprising a calibration of the means for determining the control.

The first embodiment of the process according to the invention thus makes it possible to calibrate the device according to the invention, without using an artificial eye, and in the absence of the main beam FA.

A second embodiment of the process according to the invention, implemented in the simulator according to the invention and shown in FIG. 1, comprises the following steps:
controlling the modulation means according to the modulation instruction,
positioning an eye to be examined at the output of the simulator according to the invention,
emitting the measurement light beam FC, emitting the main light beam FA, modulating the phase of the wave front of the secondary beam, according to the modulation instruction, by the modulation means MD, modulating the phase of the wave front of the main light beam FA interacting with the eye, according to a modulation instruction, the modulations of the main and measurement beams being simultaneous, measuring the phase modulation carried out by the modulation means on the secondary beam, and if the phase modulation carried out by the modulation means on the secondary beam is approximately equal to the modulation instruction, maintaining the control applied to the modulation means, or if the phase modulation carried out by the modulation means on the secondary beam differs from the modulation instruction, modifying the control applied to the modulation means.

The modification of the control can comprise a calibration of the means for determining the control. The modification of the control is carried out so as to reduce a discrepancy between the modulation instruction and the phase modulation carried out on the secondary beam. Thus, a device and a process according to the invention make it possible to verify, then to ensure, that the phase modulation carried out on the secondary beam and therefore on the main beam correspond to the modulation instruction, whatever the changes in ambient temperature and the modulation instruction.

The processing means comprise means for generating the modulation instruction, so that the modulation means, by modulating the main beam according to the modulation instruction, simulates on the main beam a static correction integral with the patient's eye, such as refractive surgery, or a correction of an aberration of the eye by a contact lens, a spectacles lens or an ocular implant.

In a variant of the second embodiment of the process according to the invention, a user inputs via input means the value for the correction that he wishes to simulate, for example to an assumed value for myopia, astigmatism of the eye, or a phase map also comprising higher-order aberrations of the eye such as coma, spherical aberration, trefoil, for example. The generation means then generates a modulation instruction. The user interacts with the patient using visual tests, typically by asking the patient if he can see clearly the test image projected onto the retina of his eye. If the patient does not obtain good results with the visual tests (i.e. if he does not see the test image projected onto the retina of his eye clearly), the user inputs a new value for the correction, until the patient obtains satisfactory results in the tests. If the patient obtains satisfactory results in the visual tests (i.e. if he clearly sees the test image projected on the retina of his eye), the user can deduce from this that the determined correction value satisfies the correction requirement for the aberrations of the eye. Thus, the device according to the invention makes it possible to simulate a correction, for example, in order to simulate a future personalized ablation operation on the cornea of the eye or in order to produce a design for corrective lenses adapted to the eye.

In order to improve the quality of the correction simulation, the device according to the invention comprises means for measuring eye aberrations that could interfere with the main beam. The means for measuring aberrations comprise the measurement means MA, the means of emission SRC of an illumination beam FE and an illumination aperture APT. When the emission means SRC are switched on, the illumination beam is emitted through the aperture APT, then through a lens L3, the beam splitter LM0, is reflected by the beam splitter LM1, then focussed by the lens L1 on the retina of the eye to form a point source emitting a diffusion light beam FD. The optical path of the illumination beam FE is shown in FIG. 2 by two em dash-dot lines.

The diffusion beam FD emerges from the eye, then travels the reverse path of the illumination beam to the beam splitter LM0. The beam splitter reflects the diffusion beam, which then passes through the optical system S1 then the beam splitter LM2. The diffusion beam then travels an optical path going from the splitter LM2 to the measurement means MA identical to that described for the secondary beam FC. The optical system S1 is arranged so that the diffusion beam FD is a substantially collimated light beam when it is intercepted by the modulation means MD. The modulation means are arranged for locally modulating the phase of the wave front of the diffusion beam FD according to the modulation instruction. The measurement means MA make it possible to measure, in the measurement plane PA, the phase of the wave front of the diffusion beam emitted by the point source. The optical path of the diffusion beam FD, going from the retina of the eye to the measurement means MA, is shown in FIG. 2 by two dotted lines. So that the measurement of aberrations can be used for the main beam FA, the wavelength of the diffusion beam FD and that of the illumination beam FE are close (within approximately 100 nanometers) to that of the main beam FA or preferably approximately equal to that of the main beam FA, and are therefore preferably situated in the visible.

The lens L1 is centred on a measurement axis z corresponding to the ocular axis of the eye in a given position, and is associated with the lenses L2 and L3 in order to provide the optical conjugation between the pupil of the eye, the plane of the illumination aperture APT and the measurement plane PA of the measurement means MA.

The processing means TRT, connected to the measurement means, provide the phase cartography of the wave FD emerging from the eye and calculate the aberrations of the eye. A representation of this cartography can be displayed on a screen SCR. Calculation of the aberrations of the eye can be carried out in a standard fashion, for example without modulating the phase of the diffusion beam by the modulation means (modulation instruction zero), and by analysing the phase cartography of the diffusion beam FD. The calculated aberrations are stored in the processing means TRT.

Preferably, measurement of the aberrations of the eye (shown in FIG. 2 in particular by beams FE and FD) is carried out in the absence of the measurement beam FC and main beam FA. When carrying out the second embodiment of the process according to the invention (shown in FIG. 1, in particular by the beams FA and FC), it is possible but not preferable to continue this measurement of aberrations, in order to limit the number of light beams interacting with the eye. Moreover, it is preferable not use the measurement beam FC and diffusion beam FD at the same time, as the phase analyzer MA can preferably analyze only one beam at a time. Thus, if the source SI is switched on, the source SRC must preferably be switched off, and vice-versa. A solution for using the measurement beam FC and diffusion beam FD at the same time is to replace the phase analyzer MA by a beam splitter and by a first and second phase analyzer, the beam splitter directing the secondary beam FC to the first phase analyzer and directing the diffusion beam FD to the second phase analyzer, the first and second phase analyzers interacting with the processing means TRT in the same way as the analyzer MA. However, this solution is not advantageous in terms of costs.

Thus, in another variant of the second embodiment of the process according to the invention, the modulation instruction is calculated by the processing means as a function of the measured and/or stored values for the aberrations of the eye, preferably to compensate for the effect of the aberrations on the main beam. A user can always adjust the modulation instruction via the input means, for example for fine adjustment of the simulation of an static correction integral with the patient's eye.

However, compensation of the aberrations of the eye is limited by the movements of the eye, lateral movements (perpendicular to the axis z) or rotation of the ocular axis, which induce variations in the aberrations of the eye at rapid frequencies of change (typically higher than 5 Hz). The device according to the invention, therefore preferably comprises means for measuring the movements of the eye as described in the document FR 2 866 551, independent of the means for measuring the aberrations of the eye. The processing means TRT are then arranged for calculating the modulation instruction as a function of measured values of the movements of the eye and measured values of the aberrations of the eye.

The means for measuring the movements of the eye comprise, for example, means for illuminating the pupil of the eye, (typically two diodes DEL not focussed on the pupil of the eye), an array detector DET, and a lens L4 forming the image IMA of the pupil of the eye on the detector. Before being projected on the detector DET, the image of the pupil of the eye passes through the lens L1 and the beam splitter LM1, the lenses L1 and L4 being arranged to conjugate the plane of the pupil of the eye with the plane of the detector DET (as shown by the virtual beam in a solid line linking the eye EYE and the detector DET in FIGS. 1 and 2). The detector is connected to the processing means TRT, which, by following the movement of the pupil of the eye, measure the lateral displacement of the pupil of the eye with respect to a predetermined position.

The means for measuring the movements of the eye can comprise moreover means (not shown) for forming at least one beam focussed in the plane of the pupil of the eye and forming a light spot on said pupil, the spot being imaged on the detector DET in the same manner as for the pupil of the eye, the processing means being arranged to determine the rotation of the eye with respect to a predetermined position, based on the relative positions of the spots with respect to the image of the pupil on the detector.

The simulator also comprises a measurement diaphragm DIA situated between the lens L2 and the beam splitter C1, and centered on the optical axis z of the different optical elements situated on the optical path of the illumination beam FE, the diffusion beam FD, and the secondary beam FC. The measurement beam FC and diffusion beam FD are substantially focussed at the centre of the measurement diaphragm DIA, and the illumination aperture APT is off-centre with respect to the optical axis z, so that only the measurement and diffusion beams are intercepted by the measurement means MA, all the other stray light fluxes being deflected away from the measurement means MA. The measurement diaphragm makes it possible in particular to filter all the stray light fluxes reflected by the cornea of the eye and any other dioptre situated between the cornea and the diaphragm DIA.

The modulation means MD, the measurement means MA, the emission means SI of the measurement light beam FC and all the optical means situated on the path of the secondary beam between the emission means SI and the measurement means MA, the light source VF and all the optical means situated on the path of the main beam between the source VF and the beam splitter LM1, the means of emission SRC of the illumination beam FE and all the optical means situated on the path of the illumination beam between the emission means SRC and the beam splitter LM1, are integral and mounted on a platform PTF1 mobile along the optical axis z of the lens L1, the focal plane of which is situated substantially in the plane of the pupil of the eye. The platform PTF1 makes it possible to adjust the focussing of the image of the test image on the retina of the eye while retaining the optical conjugation between the pupil of the eye, the plane of the illumination aperture APT and the measurement plane PA of the measurement means MA.

It should be noted that the visual simulator according to the invention can operate by sending only the main beam into the patient's eye, while ensuring, by means of the secondary beam, that the phase modulation carried out on the main beam corresponds to the modulation instruction. Thus, the visual simulator according to the invention makes it possible to ensure a satisfactory accuracy of visual simulation while limiting the patient's visual discomfort. Illumination of the eye by the emission means SRC and/or the diodes DEL for measuring the aberrations and/or movements of the eye makes it possible to calculate the instruction as a function of the aberrations and/or movements of the eye, but is optional only. Moreover, in view of the intrinsic stability of the aberrations of the eye over time, only one measurement of the aberrations of the eye is required in order for them to be known during an ophthalmic examination using the device according to the invention. Thus, the emission means SRC can be switched off and the modulation instruction can be calculated as a function of stored aberration values.

Figure 3:
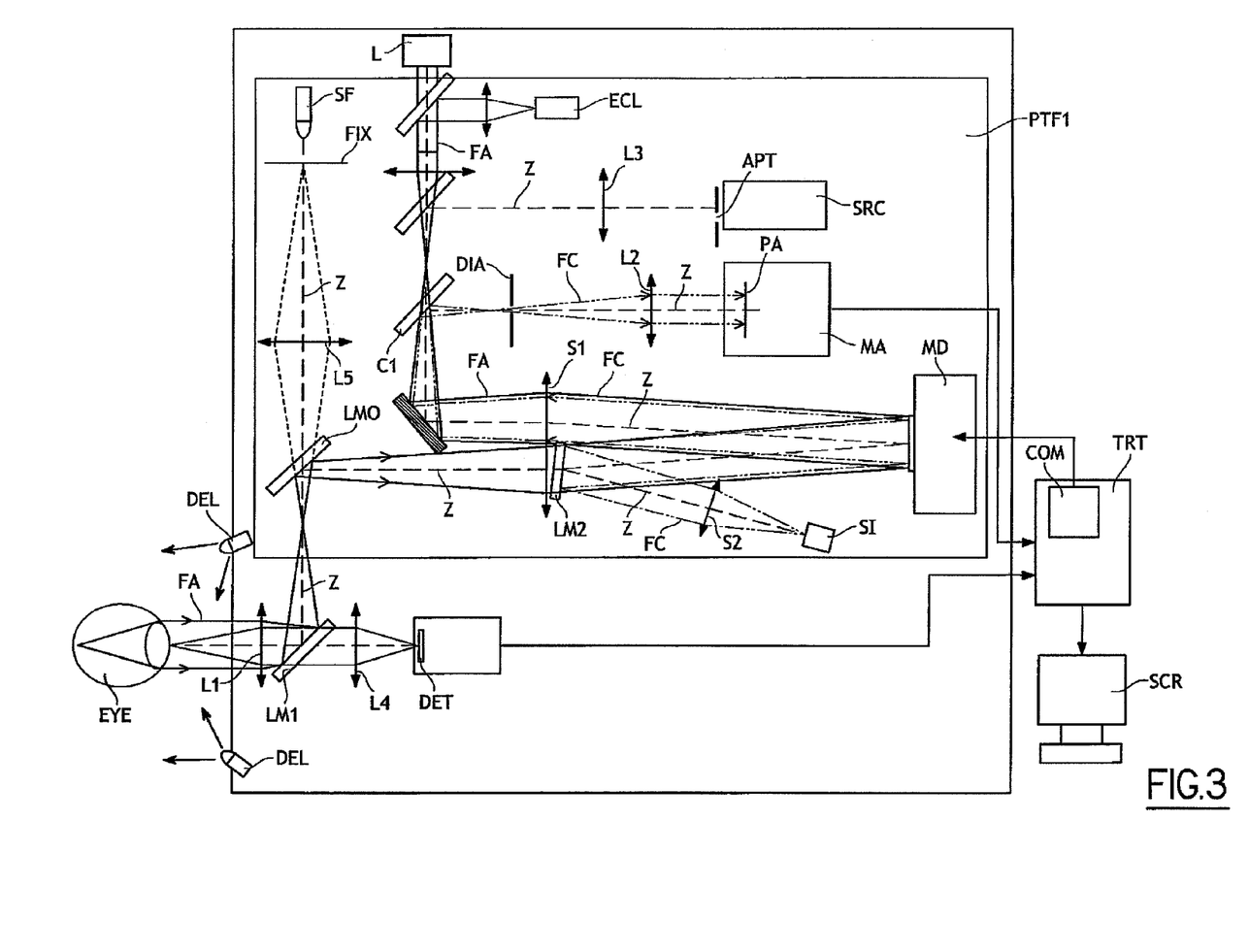
FIG. 3 shows a phase modulation device according to the invention, integrated into a retinal imaging instrument and implementing the steps of the process according to the invention.
Figure 4:
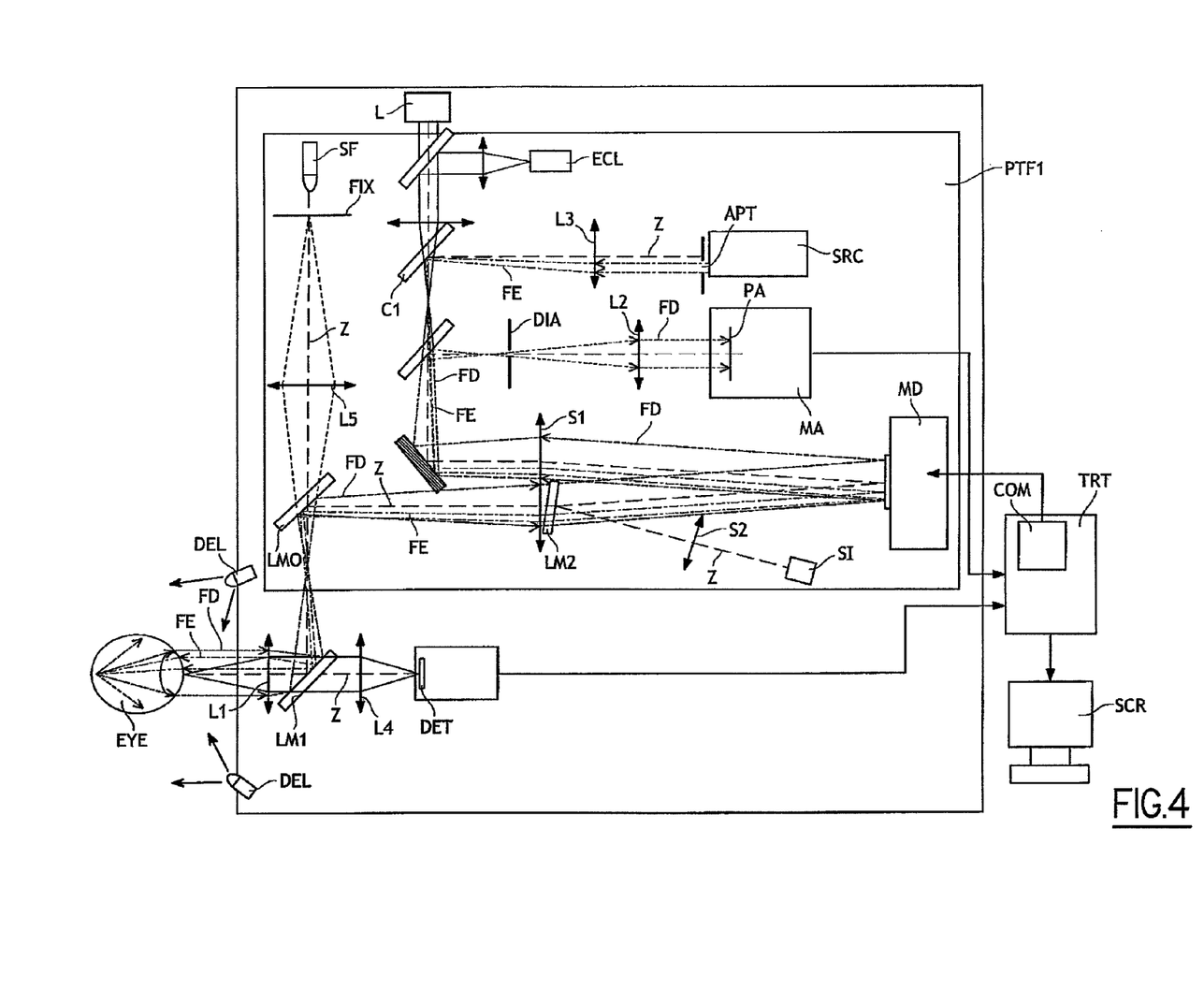
FIG. 4 shows the imaging device of FIG. 3 implementing other steps of the process according to the invention.

With reference to FIGS. 3 to 4, a phase modulation device according to the invention will now be described, integrated into a retinal imaging instrument implementing a process according to the invention. Retinal imaging instrument means any type of instrument allowing the visualization of the retina, whatever its operating process. This can be, for example, a fundus camera system, an angiography system, a Scanning Laser Ophthalmoscope (SLO) type, or Optical Coherence Tomography (OCT) type instrument.

This retinal imaging instrument according to the invention will be described insofar as it differs from the visual simulator shown in FIGS. 1 and 2. In particular, the arrangements and functions of the measurement means MA, the measurement plane PA, the lenses L1, and L2, the objective L4, the measurement diaphragm DIA, the beam splitters C1, LM0, LM1 and LM2, the optical systems S1 and S2, the phase modulation means MD, the control unit COM, the processing means TRT, the screen SCR, the emission means SI of the secondary beam FC, the detector DET, the diodes DEL and the eye EYE are the same as in the case of the vision simulator. The optical path of the secondary beam FC (represented in FIG. 3 by two em dash-dot-dot lines) is therefore the same as in the case of the visual simulator.

The main beam no longer consists of an image projected on the retina of the eye. In fact, the light source VF of the simulator is replaced by an illumination system ECL of the retina of the eye EYE making it possible to illuminate the retina over an area of which an image is required. A detector L placed at the output of the instrument receives the main beam FA, which consists of the beam back-scattered by the retina and emerging from the eye. An image of the retina is formed on the detector L, and can be visualized on the screen SCR. The optical path of the main beam FA, going from the retina of the eye to the detector L is shown in FIG. 3 by two lines in bold. The portion of the optical path of the main beam between the eye and the beam splitter C1, is common with the optical path of the main beam in the case of the vision simulator shown in FIGS. 1 and 2. The modulation means MD are therefore arranged to modulate the phase of the main beam.

A fixation path, coupled to the system by the beam splitter LM0, makes it possible to fix the attention of the patient whose eye is being analyzed and to limit eye movements. It comprises an image FIX illuminated by a light source SF and imaging means L5 ensuring the optical conjugation of the image with the retina, or regulated such that the image is seen with slight myopic defocusing in order to stimulate disaccommodation.

The imaging instrument also comprises, as in the case of the vision simulator, means for measuring aberrations of the eye comprising the measurement means MA, the means of emission SRC of the illumination beam FE, the lens L3 and the illumination aperture APT, arranged slightly differently, but with the same functions as in the case of the vision simulator. In particular, the optical conjugation between the pupil of the eye, the plane of the illumination aperture APT and the measurement plane PA of the measurement means MA is ensured by the combination of the lenses L1, L2 and L3. The illumination beam is therefore focused by the lens L1 on the retina of the eye in order to form a point source emitting a diffusion light beam FD. The optical path of the illumination beam FE, going from the emission means SRC to the retina of the eye, is shown in FIG. 4 by two em dash-dot lines. Typically, the area of the retina illuminated by the illumination system ECL is ten times greater than the size of the light point formed on the retina by the illumination beam FE, as measurement of the aberrations requires mapping the retina of the eye at a higher resolution than the image of the retina visualized on the screen SCR.

The optical path of the diffusion beam FD, which goes from the retina of the eye to the measurement means MA, is the same as in the case of the visual simulator, and is shown in FIG. 4 by two dotted lines.

The modulation means MD, the measurement means MA, the means of emission SI of the measurement light beam FC and all the optical means situated on the path of the secondary beam between the emission means SI and the measurement means MA, the light source SF and all the optical means situated on the optical path between the source SF and the beam splitter LM1, the means of emission SRC of the illumination beam FE and all the optical means situated on the path of the illumination beam between the emission means SRC and the beam splitter LM1, the illumination system ECL and the detector L are integral and mounted on a platform PTF1 mobile along the optical axis z of the lens L1 of which the focal plane is situated substantially in the plane of the pupil of the eye. The platform PTF1 makes it possible to adjust the focus of the main beam FA on the detector L while retaining the optical conjugation between the pupil of the eye, the plane of the illumination aperture APT and the measurement plane PA of the measurement means MA.

The first embodiment of the process according to the invention can be applied to the imaging instrument according to the invention, and makes it possible in particular to calibrate the means of determining the control without using an artificial eye, and in the absence of the main beam FA.

Similarly, the second embodiment of the process according to the invention can be applied to the imaging instrument according to the invention, in particular to ensure that the phase modulation carried out on the main beam corresponds to the modulation instruction. As for the vision simulator according to the invention, the processing means can calibrate the means of determining the control, and can calculate the modulation instruction as a function of correction values input on input means and/or measured or stored values for the aberrations of the eye and/or measured values of the movements of the eye, preferably for compensating on the main beam the aberrations and/or movements of the eye. The imaging instrument according to the invention can operate by illuminating the patient's eye only by the illumination means ECL, while ensuring by means of the secondary beam that the phase modulation carried out on the main beam corresponds to the modulation instruction. Illumination of the eye by the emission means SRC for measuring aberrations of the eye, by the diodes DEL for measuring the movements of the eye and by the source SF, being preferable but optional. Moreover, the emission means SRC can be switched off and the modulation instruction can be calculated as a function of stored aberration values.

In contrast to the vision simulator, the imaging instrument described above does not make it possible to simulate a correction of the eye, but makes it possible to ensure that the wave front modulation of the main beam corresponds to the modulation instruction, in order to give the phase of the main beam a shape allowing optimal performances of the instrument to be obtained.

A practical procedure for the use of an ophthalmic instrument for simulation and/or correction according to the invention will now be disclosed:

Step 1. A first step relates to a measurement of aberrations with the retinal illumination source switched on, according to the standard aberrometry procedure as disclosed in the document FR 2 866 551;

Step 2. In a second step, the position of the pupil of the eye during the measurement of the aberrations (step 1) is determined using the pupil tracking camera;

Step 3. There follows a step of switching off the retinal illumination source: the subject views the target without being disturbed by another source;

Step 4. The secondary light beam source is then switched on. This secondary beam passes over the deformable mirror before being analyzed by the wave front analyzer, and can therefore be used in the stage of closed loop enslaving the deformable mirror;

Step 5. There follows an application of the correction on the deformable mirror in a closed loop of the correction (or the simulation phase map or both). The secondary light beam is used for this step, and thus no light is directed into the patient's eye, who therefore views the target without discomfort. In order to be effective, the correction (and/or simulation) must "track" the movement of the pupil of the patient's eye. Measurement of the displacement of the pupil is carried out using the pupil tracking system, and the displacement information is used by the correction (and/or simulation) algorithm in order to generate said correction (and/or simulation) in the right position on the deformable mirror.

Step 6. Concomitantly with step 5, the patient (and the practitioner) can measure subjectively the effect of the correction or simulation on the visual perception using the fixation target, which can be a micro-display, —produced for example using an OLED (Organic Light Emitting Diode), LCD (Liquid Crystal Display) or MEMS (Micro Electro Mechanical Systems) technology—, on which different images or visual tests can be displayed (tests of visual acuity for example).

One can also provide an additional step 0 corresponding to the learning step and a step 0bis corresponding to overcoming the aberrations of the optical system of the ophthalmic instrument, using the secondary beam passing via the deformable mirror and analyzed by the analyzer. This overcoming step 0bis can consist of an enslavement of the deformable mirror in relation to an instruction correcting all the aberrations of the optical system. Thus in step 1 above, the analyzer directly measures the ocular aberrations.

Of course, the invention is not limited to the examples which have just been described, and numerous adjustments can be made to these examples without exceeding the scope of the invention.

In particular, it would also have been possible to envision the case of an optical treatment instrument, identical to the imaging instrument shown in FIGS. 3 and 4, but in which the detector L is replaced by a laser source. In this case, the main beam then consists of the beam emitted by the laser source and travels an optical path opposite to that of the main beam of the imaging instrument according to the invention.

Further, the lenses L1, L2, L3, etc. of the ophthalmic instruments described above can be replaced by more complex imaging means comprising, for example, combinations of lenses.

The invention claimed is:

1. A phase modulation device implemented in an ophthalmic instrument using a main light beam interacting with an eye, comprising:
    means for modulating the phase of the wave front of said main light beam;
    means for controlling said phase modulation means following a modulation instruction;
    means for analyzing the thus-performed modulation of the phase of the wave front of said main light beam; and
    means for emitting a secondary light beam, means for directing said secondary light beam along an optical path to said modulation means, then to said wave front analysis means, and in that said optical path does not pass through the eye, and in that the control means and wave front analysis means receiving said modulated secondary light beam cooperate, during a stage called a learning stage, to supply data regarding the response of the phase modulation means to a set of predetermined modulation instructions.

2. The device according to claim 1, in which the phase modulation means comprises a deformable mirror actuated by a plurality of actuators, wherein, in a learning stage, the wave front analysis means and control means cooperate in order to set each actuator successively in motion and to store, for each actuator, the response of said wave front analysis means.

3. The device according to claim 1, further comprising means for modifying the control applied to the modulation means, in order to reduce a discrepancy between the modulation instruction and the modulation carried out on the secondary light beam.

4. The device according to claim 1, wherein the optical path along which the secondary beam is guided is internal to the ophthalmic instrument.

5. The device according to claim wherein a wavelength of the secondary beam is approximately equal to a wavelength of the main beam.

6. The device according to claim 1, wherein the modulation means are arranged in order to modulate, according to a modulation instruction, the phase of the wave front of the main beam and the phase of the wave front of the secondary light beam simultaneously.

7. The device according to claim 1, further comprising means for projecting an image of a target onto a retina of the eye.

8. The device according to claim 7, wherein the light rays originating from the target constitute the main beam.

9. An ophthalmic instrument, of the visual simulator type, comprising a phase modulation device according to claim 7, wherein the modulation means are controlled in order to simulate on the main beam a static correction integral with the eye, such as refractive surgery, or a correction by a contact lens, a spectacles lens or an ocular implant.

10. A retinal imaging instrument comprising a phase modulation device according to claim 1, further comprising means for illuminating a retina of the eye, means for detecting a light beam emerging from the eye and for forming an image of the retina, said emergent beam constituting the main beam.

11. An instrument for optical treatment of the retina of the eye, comprising a phase modulation device according to claim 1, further comprising a laser source for emitting the main beam, and means for focusing the main beam onto the retina of the eye.

12. An instrument for aberrometry of the eye, comprising a phase modulation device according to claim 1, further comprising means for measuring aberrations of the eye liable to interfere with the main beam, and means for calculating the modulation instruction as a function of measured values of the aberrations of the eye.

13. The instrument according to claim 12, wherein the means for measuring aberrations of the eye comprise means of emission of an illumination beam in order to form a secondary light source on the retina of the eye, said secondary source emitting a beam which emerges from the eye, and means for guiding said beam to means of measurement of the phase of the wave front of said beam.

14. An ophthalmic instrument comprising a modulation device according to claim 1, further comprising means for measuring movements of the eye, and means for calculating the modulation instruction as a function of measured values of the movements of the eye.

15. The instrument according to claim 14, wherein the means for measuring movements of the eye include means for measuring a lateral displacement of the pupil of the eye with respect to a predetermined position.

16. The instrument according to claim 14, wherein the means for measuring the movements of the pupil of the eye comprise means of illuminating the pupil of the eye, an array detector, and an objective forming the image of the pupil of the eye on the detector.

17. The instrument according to claim 14, wherein the means for measuring movements of the eye comprise means for measuring a rotation of the eye with respect to a predetermined position.

18. The instrument according to claim 14, wherein the means for measuring the movements of the eye comprise an array detector, an objective forming the image of the pupil of the eye on the detector, means for forming at least one beam substantially focused in the plane of the pupil of the eye and forming a light spot on said pupil, and means for determining the rotation of the eye from the relative positions of the spot with respect to the image of the pupil.

19. A process for calibrating an ophthalmic device using a main light beam interacting with an eye for implementing: (i) a phase modulation of the wave front of said main light beam by phase modulation means and (ii) an analysis of said wave front phase modulated in this way by phase analysis means, comprising, during a stage called a learning stage:
    emitting a secondary light beam which is subjected to said phase modulation then to said phase analysis; and
    a sequence of predetermined controls of said phase modulation means, and storage of phase analysis data in response to said modulation controls;

wherein the secondary light beam is directed along an optical path to said modulation means and to said phase analysis means, and said optical path does not pass through the eye.

20. The process according to claim 19, implemented in a device in which the phase modulation means comprises a mirror which can be deformed by the action of a plurality of actuators, wherein the sequence of predetermined controls comprises controls for successively starting each actuator to move and for storing, for each actuator, the response of said wave front analysis means.

21. The process according to claim 19, further comprising a modulation of the control applied to the modulation means, so as to reduce a discrepancy between the modulation instruction and the modulation carried out on the secondary beam.

22. The process according to claim 19, further comprising guiding the beam along an optical path so that the secondary beam does not interact with the eye.

23. The process according to claim 19, further comprising a simultaneous modulation of the phase of the wave front of the main beam and the phase of the wave front of the secondary beam.

24. The process according to claim 19, implemented in an ophthalmic instrument comprising a primary source for generating a main light beam for illuminating a retina of an eye and a second source for generating a secondary light beam, further comprising:

a step of measuring the aberrations of the optical system of said ophthalmic instrument, said primary source of illumination of the retina being switched on, a step of determining the position of the pupil of the eye during said step of measurement of the aberrations, a step of switching off said primary source of illumination of the retina, a step of starting said second source for generating the secondary beam, said secondary beam being used in the learning stage, and a step of applying correction and/or simulation controls to the phase modulation means.

25. The process according to claim 24, further comprising implementing a fixation target, such as a micro-display, on which visual tests or images can be displayed, said fixation target being provided to give a patient a subjective measure of the effect of the correction and/or the simulation.

26. The process according to claim 24, further comprising, prior to the step of measuring the aberrations, an initial learning step and a step of overcoming the aberrations of the optical system of the ophthalmic instrument.

27. The process according to claim 26, further comprising the step of overcoming the aberrations of the optical system comprises an enslavement of the phase modulation means with respect to a determined instruction, in order to correct the aberrations of said optical system.

* * * * *